United States Patent [19]

Sato

[11] 4,108,984

[45] Aug. 22, 1978

[54] COMPOSITIONS AND METHODS FOR THE TREATMENT OF ATHLETE'S FOOT

[76] Inventor: Masataro Sato, No. 28-26 Fukuokamachi 2-chome, Takamasatu, Japan

[21] Appl. No.: 759,492

[22] Filed: Jan. 14, 1977

[51] Int. Cl.² .............................................. A61K 37/48
[52] U.S. Cl. ........................................ 424/94; 424/46; 424/61; 424/65; 424/69; 424/154; 424/155
[58] Field of Search ................... 424/94, 155, 154, 46, 424/61, 65, 69

[56] References Cited

FOREIGN PATENT DOCUMENTS

| | | | |
|---|---|---|---|
| 105,815 | 11/1938 | Australia | 424/69 |
| 2,201,880 | 7/1974 | France | 424/65 |
| 2,307,479 | 8/1974 | Fed. Rep. of Germany | 424/65 |
| 7,824 of | 1907 | United Kingdom | 424/69 |
| 514,979 | 11/1939 | United Kingdom | 424/65 |
| 926,517 | 5/1963 | United Kingdom | 424/94 |

OTHER PUBLICATIONS

Chemical Abstracts, vol. 68: 10549d (1968), vol. 26: p. 4127 (1932) & vol. 17: p. 2104 (1911).
The Dispensatory of the U.S.A. 24th Ed. (1947), published by J. B. Lippincott Co., Phila. Pa., pp. 10, 11, 140–141, 818, 819, pp. 1520–1521.
Scientific American, Jun. 1960 (Fleming's Lysozyme), pp. 132–133, 134, 136–138 & 140–142.
Soil Science, Feb. 1954, pp. 129–137.

*Primary Examiner*—Donald B. Moyer
*Attorney, Agent, or Firm*—Browdy & Neimark

[57] ABSTRACT

Montmorillonite, either alone or when combined with other materials, is highly effective in the treatment of dermatomycosis pedis. Even better results are obtained when the composition contains about 80% montmorillonite, about 20% pyroligneous acid and a very small quantity of papain enzyme. About 0.5% of lysozyme hydrochloride may also be added. The compositions are not only effective for the treatment of both wet and dry athlete's foot, but also in deodorizing the unpleasant odors of socks and the inside of shoes.

4 Claims, No Drawings

COMPOSITIONS AND METHODS FOR THE TREATMENT OF ATHLETE'S FOOT

FIELD OF THE INVENTION

The present invention relates to compositions and methods for curing dermatomycosis pedis (hereinafter referred to as athlete's foot) and more particularly to such methods and compositions using montmorillonite as principal ingredient.

BACKGROUND OF THE INVENTION

Athlete's foot is a chronic superficial fungal infection of the skin of the foot, especially of that between the toes and on the soles. It is usually caused by species of Trichophyton or by *Epidermophyton floccosum* or *Candida albicans*. Athlete's foot may be of different types and degrees of severity and may be marked by maceration, cracking and scaling of the skin, and by intense itching.

In the past many types of athlete's foot have been cured by applying acid liquid or ointment. If the ailment is not a serious one, use of vinegar proves to be effective to some extent. However, while these known medicaments are somewhat effective for the cure of dry athlete's foot, they are not particularly efficacious against wet athlete's foot.

Wet type athlete's foot is most fertile and resistant. Mankind has most probably been tortured by this ailment ever since the dawn of the history of mankind, without there ever being a decisive curative means against this type of athlete's foot.

Dampness is an anathema to wet athlete's foot. Therefore ointments or liquid medicines when applied for cure of such wet athlete's foot, give moisture to the ailing part and cannot produce satisfactory curative effect such as is obtained when they are used for cure of dry athlete's foot.

For the treatment of wet athlete's foot there are currently employed methods in which a dry athlete's foot curative ointment is first applied to the affected part and then air is immediately blown thereonto to dry the ointment-applied part, or talc or such is spread thereover to absorb moisture to thereby dry said part.

However, this type of medicament naturally contains moisture which is most undesirable for the treatment of wet athlete's foot, so that such medicament gives dampness, if temporarily, to the ailing part upon every application thereof. Therefore, such medicament cannot always produce a satisfactory curative effect. Furthermore, the method of application is rather troublesome.

The most ideal medicament for the remedy of wet athlete's foot would be one which is acidic in nature and can well absorb moisture to keep the ailing part dry.

SUMMARY OF THE INVENTION

It is accordingly an object of the present invention to eliminate these problems found in the prior art. It is another object of the present invention to produce a medicament which can be used for both wet and dry athlete's foot.

It is yet another object of the present invention to produce a medicament which is acidic in nature and can well absorb moisture to keep the ailing part dry.

It is yet another object of the present invetion to provide a method for the treatment of athlete's foot using such a medicament.

It is still another object of the present invention to provide a composition which deodorizes odors from socks and the inside of shoes.

As a result of many years study on this subject, a material which meets these requirements has been discovered. This material is montmorillonite.

It has been found further that montmorillonite is even more effective when mixed in a weight ratio of approximately 4–1 with pyroligneous acid and a very small amount of papain enzyme.

DETAILED DESCRIPTION OF PREFERRED EMBODIMENTS

Montmorillonite is a clay mineral having the following outstanding physical/chemical properties:

Its absorptivity is several times as high as active carbon; it is able to absorb more than 20 times as much moisture as its own weight; and it has a base substituting action.

For practical use, montmorillonite is merely dried under heating and then pulverized and prepared into a fine powder. When the thus prepared medicament of the present invention is simply applied to the ailing part, the following peculiar effects are produced:

(a) The applied medicament is quick to dry.
(b) It penetrates quickly and extensively.
(c) It forms athe crust rapidly and causes prompt descrustation.

The results of many clinical experiments have assured quick drying and cure of even wet athlete's foot owing to these peculiar effects of the material of the present invention.

In the clinical tests of the present invention, montmorillonite which is found in the neiborhood of Sentsumachi, Mima-gun, Tottori-ken or Shimane-ken, Japan was used. This montmorillonite has the following chemical composition: 70% of silicic acid, 16.5% of alumina, 8.6% of water of crystallization, 1.94% of magnesium, 1.4% of iron oxide, and minute quantities of calcium oxide, manganese oxide and the like.

In use for treatment of wet athlete's foot, it suffices to apply a suitable quantity of this powdery preparation to the effective part, several days apart. If the ailment is slight, it may be cured with only one application of the preparation. However, even a serious case can be completely cured by 7–8 timely applications.

As this medicament is composed of a natural mineral, it can be provided at very low cost. Furthermore, it has no toxicity and no side effects and yet has splendid remedial effect against wet athlete's foot.

In a study of many clinical experiments for elevating even more the remedial efficacy of montmorillonite and preparing a medicament which has powerful curative effect against wet athlete's foot, it has been discovered that if montmorillonite is added with certain specific materials in certain specified amount ranges, there is produced an effect several times as high as when montmorillonite is used singly. The specific materials found to have this effect when added to montmorillonite are pyroligneous acid and papain enzyme.

Pyroligneous acid is a by-product, together with tar, of the dry distillation of wood. It is composed mainly of acetic acid and contains methanol, acetone, methyl acetate, etc. as minor ingredients. It has high permeability and bactericidal activity.

Papain enzyme is obtained by drying juice of unriped papaya fruit, and it contains papain, chymopapain, protease (proteolytic enzyme) and the like.

Each of the ingredients of this improved composition, montmorillonite, pyroligneous acid and papain enzyme, if used singly, demonstrates a certain remedial effect against athlete's foot, but it has been ascertained from clinical experiments that if these three materials are mixed together at a certain ratio, there is produced not a simple additive action but in fact a synergistic effect. The detailed mechanism of such effect and the interrelation of these three components is still not completely understood, and must await further scientific research.

EXAMPLE

Montmorillonite is mixed under agitation with pyroligneous acid in a weight ratio of 4 to 1, and the mixture is dried under heating and refined into fine powder. Papain enzyme is then added in an amount of 1/5000 of the mixture weight. When the thus obtained medicament is applied to a foot suffering from wet athlete's foot, which is considered an intractable cutaneous ailment, drying and contration of the affected part is observed from the day after application, and if the ailment is slight, it can be completely cured with one application of the medicament.

Usually, it suffices to apply a suitable amount of the medicament to the affected part several days apart, and even if the ailment is serious, it can be cured by repeating application 5 to 6 times at suitable time intervals. When applied to the dermatomycosis pedis bacilli haunting below the outer layer of the skin in the winter season, the preparation of the present invention can penetrate there in several minutes to give urtication with some pain to the patient, and a scab is formed on the affected part in several days. If such scab is left as is without stripping it off forcibly, the dead bacilli deposit on the desquamated cuticles and come off by themselves.

Lysozyme hydrochloride may be added to the above preparation in an amount of approximately 0.5%. It produces the additional effects of preventing expansion of the ailment and also destroying the bad odor of the socks or in the shoe.

The improved composition of the present invention containing montmorillonite and pyroligneous acid, with a small amount of papain and the optional addition of lysozyme hydrochloride can be produced at a very low cost and has no toxicity or side effects and yet produces outstanding curative effects as described hereinabove.

It will be obvious to those skilled in the art that various changes may be made without departing from the scope of the invention and the invention is not to be considered limited to what is described in the specification.

What is claimed is:

1. A method for treating wet athlete's foot on a patient in need of said therapy comprising applying a dry mixture of (1) montmorillonite in finely powdered form with (2) pyroligneous acid in a weight ratio of 4 to 1 and (3) a very small quantity of papain enzyme to the affected area in an amount sufficient to keep the affected area dry and to ameliorate the wet athlete's foot.

2. A method in accordance with claim 1 wherein said papain enzyme is present in an amount of about 1/5000 by weight of the mixture.

3. A method in accordance with claim 1 wherein said mixture further includes about 0.5% of lysozyme hydrochloride.

4. A composition for the treatment of dermatomycosis pedis comprising a dry mixture of finely powdered montmorillonite and pyroligneous acid in a weight ratio of about 4 to 1, a small quantity of papain enzyme present in an amount of about 1/5000 by weight of the mixture, and further including about 0.5% of lysozyme hydrochloride.

* * * * *